(12) United States Patent
Heraty et al.

(10) Patent No.: US 9,883,961 B2
(45) Date of Patent: Feb. 6, 2018

(54) MEDICAL DEVICE

(75) Inventors: Kevin Heraty, County Mayo (IE);
Liam Mullins, County Westmeath (IE);
Paul Gilson, County Galway (IE);
Martin Burke, County Galway (IE);
Ray Blowick, Galway (IE)

(73) Assignee: Veryan Medical Limited, Oxford (GB)

( * ) Notice: Subject to any disclaimer, the term of this patent is extended or adjusted under 35 U.S.C. 154(b) by 39 days.

(21) Appl. No.: 13/123,113

(22) PCT Filed: Oct. 12, 2009

(86) PCT No.: PCT/GB2009/002433
§ 371 (c)(1),
(2), (4) Date: Jun. 28, 2011

(87) PCT Pub. No.: WO2010/041038
PCT Pub. Date: Apr. 15, 2010

(65) Prior Publication Data
US 2011/0257673 A1 Oct. 20, 2011

Related U.S. Application Data

(63) Continuation-in-part of application No. 12/249,448, filed on Oct. 10, 2008, now Pat. No. 9,597,214.

(30) Foreign Application Priority Data

Oct. 10, 2008 (EP) .................................. 08253309

(51) Int. Cl.
*A61F 2/82* (2013.01)
*A61F 2/958* (2013.01)
(Continued)

(52) U.S. Cl.
CPC ........ *A61F 2/958* (2013.01); *A61F 2002/068* (2013.01); *A61F 2002/3008* (2013.01);
(Continued)

(58) Field of Classification Search
CPC ........................................................ A61F 2/82
(Continued)

(56) References Cited

U.S. PATENT DOCUMENTS 4,596,548 A 6/1986 DeVries et al.
4,604,762 A 8/1986 Robinson
(Continued)

FOREIGN PATENT DOCUMENTS

EP 0 275 230 7/1988
EP 0 696 447 A2 2/1996
(Continued)

OTHER PUBLICATIONS

Min Invas Ther & Allied Technol 2002: 11(4) pp. 173-178, Entitled: A Comparison of Balloon- and Self-Expanding Stents.
(Continued)

*Primary Examiner* — Matthew Schall
(74) *Attorney, Agent, or Firm* — Fay Sharpe LLP

(57) ABSTRACT

A medical device includes an expandable element for location in a blood vessel. The expandable element is movable between a collapsed configuration and an expanded configuration. In the expanded configuration, at least a part of a longitudinal axis of the expandable element is curved in three-dimensional space. The medical device can be stent deployment device which includes an elongate catheter shaft and an inflatable balloon.

18 Claims, 14 Drawing Sheets

(51) Int. Cl.
 A61F 2/06 (2013.01)
 A61F 2/30 (2006.01)
 A61M 25/10 (2013.01)

(52) U.S. Cl.
 CPC .............. *A61F 2002/30289* (2013.01); *A61F 2230/0091* (2013.01); *A61F 2250/0098* (2013.01); *A61M 25/1011* (2013.01)

(58) Field of Classification Search
 USPC ........................................................ 623/1.11
 See application file for complete search history.

(56) References Cited

U.S. PATENT DOCUMENTS

| | | | |
|---|---|---|---|
| 5,156,619 | A | 10/1992 | Ehrenfeld |
| 5,295,959 | A | 3/1994 | Gurbel et al. |
| 5,308,356 | A | 5/1994 | Blackshear, Jr. et al. |
| 5,370,691 | A | 12/1994 | Samson |
| 5,383,856 | A | 1/1995 | Bersin |
| 5,409,458 | A | 4/1995 | Khairkhahan et al. |
| 5,484,411 | A | 1/1996 | Inderbitzen et al. |
| 5,545,132 | A | 8/1996 | Fagan et al. |
| 5,569,191 | A | 10/1996 | Meyer |
| 5,596,990 | A | 1/1997 | Yock et al. |
| 5,618,299 | A | 4/1997 | Khosravi et al. |
| 5,649,978 | A | 7/1997 | Samson |
| 5,653,745 | A | 8/1997 | Trescony et al. |
| 5,670,161 | A | 9/1997 | Healy et al. |
| 5,733,327 | A | 3/1998 | Igaki et al. |
| 5,735,816 | A | 4/1998 | Lieber et al. |
| 5,800,456 | A | 9/1998 | Maeda et al. |
| 5,865,723 | A | 2/1999 | Love |
| 6,039,754 | A | 3/2000 | Caro |
| 6,152,139 | A | 11/2000 | Laufer |
| 6,364,904 | B1 | 4/2002 | Smith |
| 6,375,660 | B1 | 4/2002 | Fischell |
| 6,425,908 | B2 | 7/2002 | Ravenscroft et al. |
| 6,527,739 | B1 | 3/2003 | Bigus et al. |
| 6,569,191 | B1 | 5/2003 | Hogan |
| 6,896,007 | B2 | 5/2005 | Cymbalisty |
| 7,766,871 | B2 * | 8/2010 | Hirszowicz et al. .... 604/103.07 |
| 2001/0049549 | A1 | 12/2001 | Boylan et al. |
| 2002/0022877 | A1 | 2/2002 | Mueller et al. |
| 2002/0035390 | A1 | 3/2002 | Schaldach et al. |
| 2002/0049487 | A1 | 4/2002 | Lootz et al. |
| 2002/0077693 | A1 | 6/2002 | Barclay et al. |
| 2002/0116044 | A1 | 8/2002 | Cottone |
| 2002/0179166 | A1 | 12/2002 | Houston et al. |
| 2003/0163154 | A1 | 8/2003 | Miyata et al. |
| 2004/0039443 | A1 | 2/2004 | Solem et al. |
| 2006/0047334 | A1 | 3/2006 | Houston et al. |
| 2006/0122554 | A1 | 6/2006 | Wilk |
| 2006/0124187 | A1 | 6/2006 | Houston et al. |
| 2007/0112407 | A1 | 5/2007 | Mertens et al. |
| 2007/0156078 | A1 | 7/2007 | Caro et al. |
| 2007/0213663 | A1 | 9/2007 | Wang |
| 2008/0306440 | A1 | 12/2008 | Hirszowicz et al. |

FOREIGN PATENT DOCUMENTS

| | | |
|---|---|---|
| EP | 0 699 423 A2 | 3/1996 |
| EP | 0 714 640 | 6/1996 |
| EP | 0 581 900 | 2/1998 |
| EP | 0 612 536 B1 | 12/1999 |
| EP | 1 042 997 A1 | 10/2000 |
| EP | 1 127 557 A1 | 8/2001 |
| EP | 1254645 A1 | 11/2002 |
| EP | 1 269 935 A2 | 1/2003 |
| EP | 1 270 040 | 1/2003 |
| EP | 1 279 382 | 1/2003 |
| EP | 2 292 183 A1 | 3/2011 |
| FR | 2 248 015 A1 | 5/1975 |
| FR | 2 657 945 A3 | 8/1991 |
| FR | 2 666 502 A1 | 3/1992 |
| GB | 2 092 894 A | 8/1982 |
| GB | 2 298 577 A | 9/1996 |
| GB | 2 344 053 A | 5/2000 |
| GB | 2 425 485 | 11/2006 |
| JP | 07-507697 | 8/1995 |
| JP | 08-215317 | 8/1996 |
| JP | 08-257139 | 10/1996 |
| JP | H11-506628 A | 6/1999 |
| JP | 2001-252987 | 9/2001 |
| JP | 2003-528689 A | 9/2003 |
| JP | 2005-103321 A | 4/2005 |
| JP | 2006-520630 | 9/2006 |
| WO | WO 95/09585 A1 | 4/1995 |
| WO | WO 95/17223 A1 | 6/1995 |
| WO | WO 95/35072 A2 | 12/1995 |
| WO | WO 97/24081 A1 | 7/1997 |
| WO | WO 98/26731 A2 | 6/1998 |
| WO | WO 98/26731 A3 | 6/1998 |
| WO | WO 98/53764 A2 | 12/1998 |
| WO | WO 99/17682 A1 | 4/1999 |
| WO | WO 00/32241 A1 | 6/2000 |
| WO | WO 00/38591 A | 7/2000 |
| WO | WO 00/38591 A2 | 7/2000 |
| WO | WO 00/38591 A3 | 7/2000 |
| WO | WO 00/48530 | 8/2000 |
| WO | WO 00/49973 A2 | 8/2000 |
| WO | WO 01/45593 A1 | 6/2001 |
| WO | WO 01/74270 A2 | 10/2001 |
| WO | WO 01/89420 A2 | 11/2001 |
| WO | WO 02/066095 | 8/2002 |
| WO | WO 02/098325 A2 | 12/2002 |
| WO | WO 03/000157 A1 | 1/2003 |
| WO | WO 03/045278 A1 | 6/2003 |
| WO | WO 03/103540 A1 | 12/2003 |
| WO | WO 2004/047908 A2 | 6/2004 |
| WO | WO 2004/066852 A2 | 8/2004 |
| WO | WO 2004/082533 | 9/2004 |
| WO | WO 2008/117256 | 10/2008 |

OTHER PUBLICATIONS

Min Invas Ther & Allied Technol 2002: 11(4) pp. 137-147, Entitled: A Survey of Stent Designs.
Eur. J. Vasc. Endovasc. Surg 24, pp. 13-22 (2002), Entitled: External Supports and the Prevention of Neointima Formation in Vein Grafts.
European Search Report of corresponding European Application No. EP 10 01 0780 dated Dec. 9, 2010.
European Search Report corresponding to EP 08 25 3309, dated Jan. 19, 2009 (English Text).
International Search Report of International Application No. PCT/GB2009/002433 dated Jan. 19, 2010 (English Text).
Written Opinion of the International Searching Authority of International Application No. PCT/GB2009/002433 dated Jan. 19, 2010 (English Text).
Abstract of Caro et al., "Influence of Non-Planar Geometry on Flow Separation" (1998) J. Physiol. 513P, 2P.

* cited by examiner

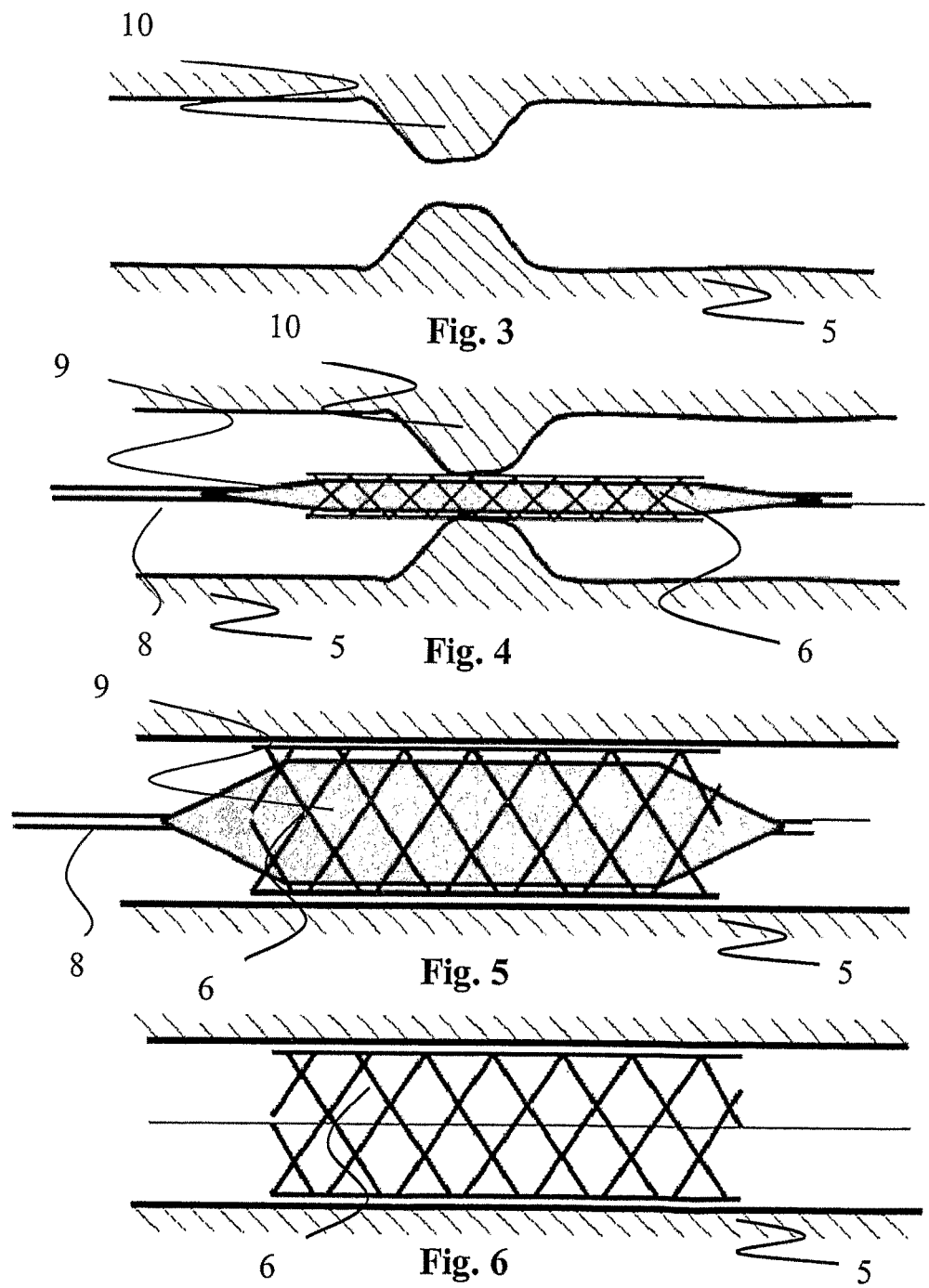

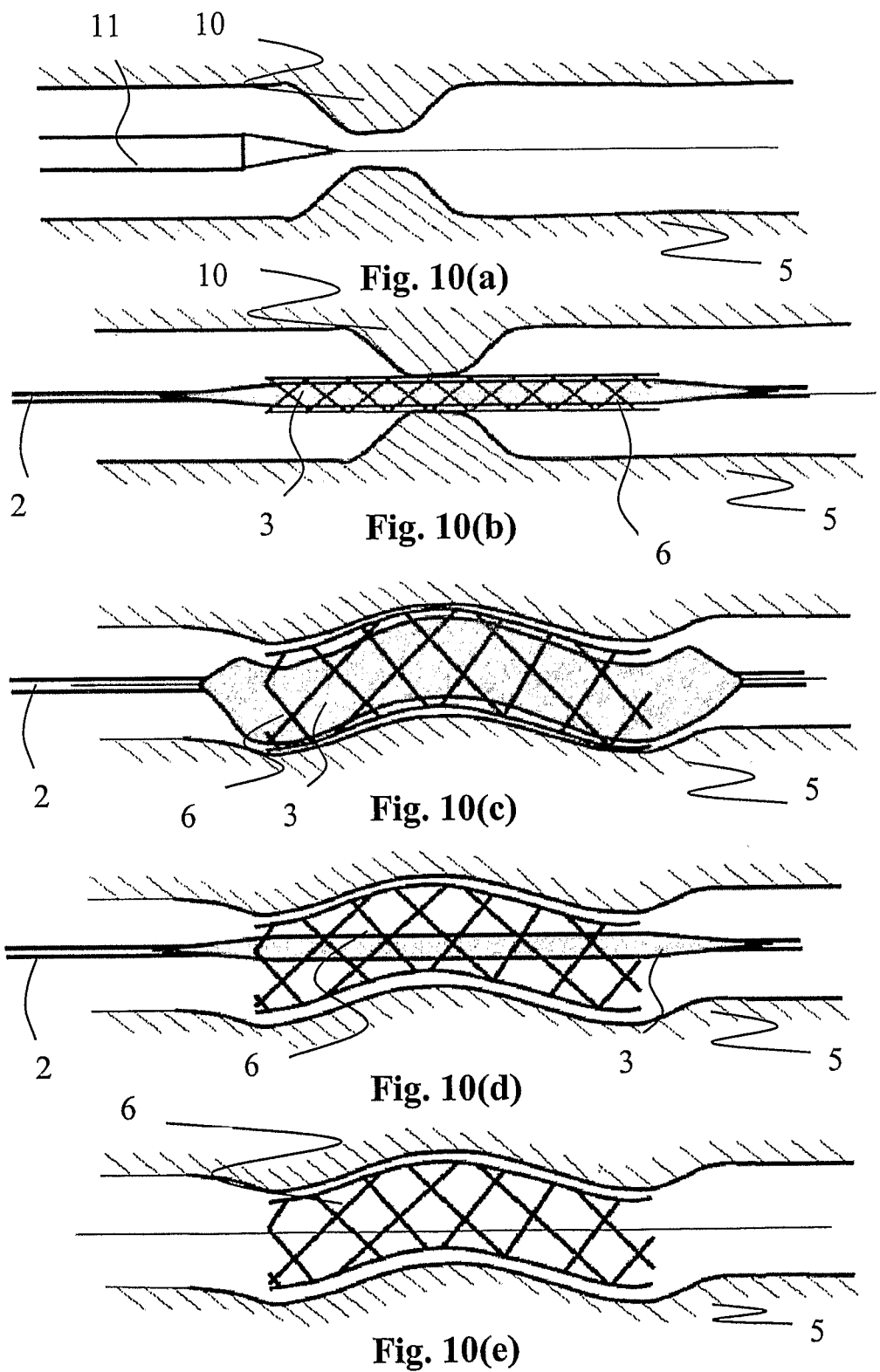

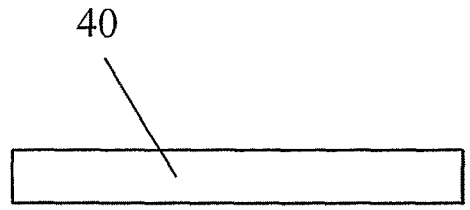
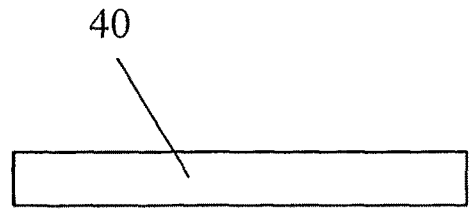
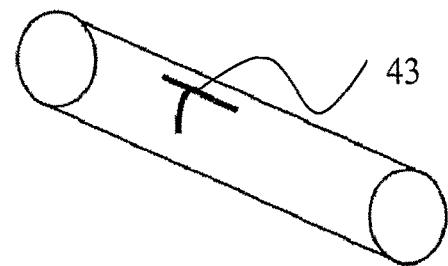
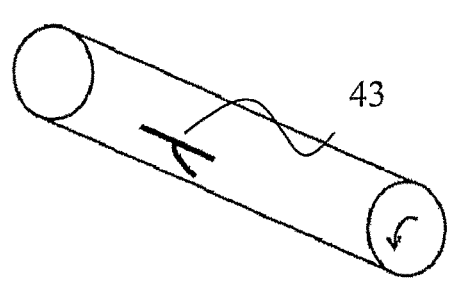
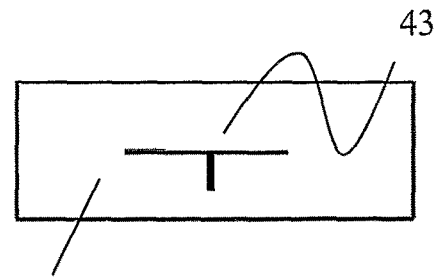
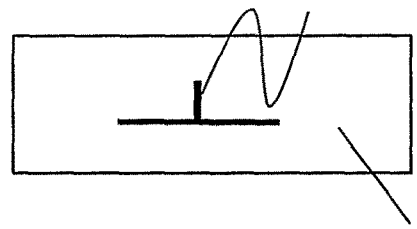
Fig. 26                    Fig. 27

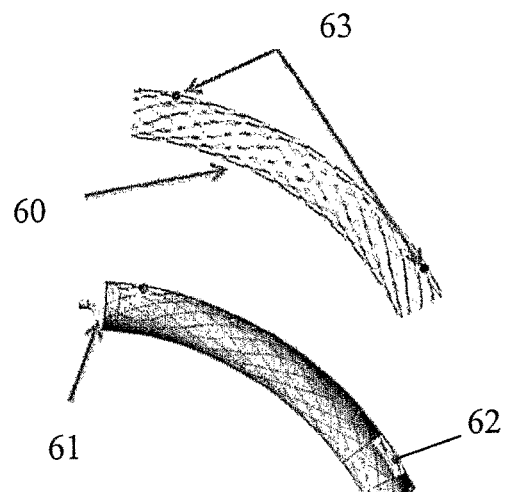
Fig. 30(a)
Fig. 30(b)
Fig. 30(c)
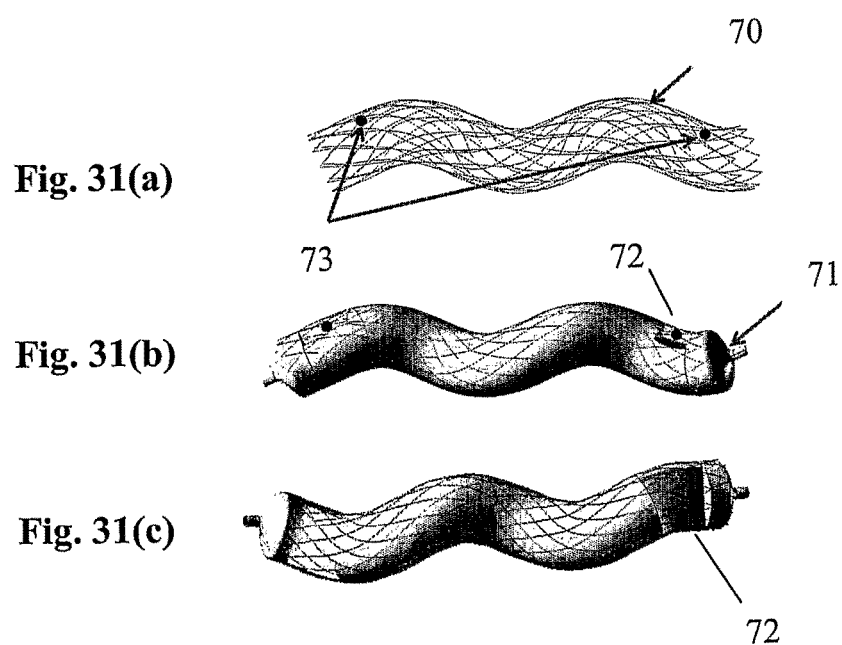
Fig. 31(a)
Fig. 31(b)
Fig. 31(c)

MEDICAL DEVICE

This application claims priority from U.S. application Ser. No. 12/249,448 which was filed on Oct. 10, 2008 and is still pending. The subject matter of that application is incorporated herein by reference in its entirety.

INTRODUCTION

This invention relates to a medical device.

STATEMENTS OF INVENTION

According to the invention there is provided a medical device comprising:—
an expandable element for location in a blood vessel,
the expandable element being movable between a collapsed configuration and an expanded configuration,
in the expanded configuration at least part of the longitudinal axis of the expandable element being curved in three-dimensional space.

In one embodiment of the invention in the expanded configuration the expandable element is configured to exert force on the internal wall of a blood vessel causing the longitudinal axis of the blood vessel to curve in three-dimensional space. Blood flowing through the three-dimensional curved part of the blood vessel undergoes a swirling action. The swirling flow of blood has been found to minimise thrombosis and platelet adhesion, and to minimise or prevent coverage of a stent by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia. Preferably the device comprises a single expandable element. However the device may alternatively comprise a plurality of separate expandable members.

In one case in the collapsed configuration at least part of the longitudinal axis of the expandable element is substantially straight. This arrangement provides a low-profile for ease of delivery. Preferably in the collapsed configuration at least part of the expandable element is substantially cylindrically shaped. In the expanded configuration at least part of the expandable element may be substantially helically shaped. In the expanded configuration at least part of the expandable element may be substantially spiral shaped.

In some preferred embodiments, at least one longitudinal end part of the expandable element has a helical angle which varies along the length of the end part. Both longitudinal end parts may have this configuration. In certain embodiments the helical angle of the longitudinal axis of an end part of the expandable element increases in a direction away from the end of the element. When a blood vessel is caused by such an expandable element to have a helical longitudinal axis, the end part of the expandable element causes the helical angle of the longitudinal axis of the blood vessel to increase along the length of the end part. Thus a transitional region may be provided in the vessel in which flow in the part of the vessel shaped by the end part of the expandable element is conditioned by the varying helical angle. This arrangement can serve to reduce the area of the internal wall of the blood vessel which has low wall shear stress, to reduce the possibility of recirculation, and to reduce the risk of neointimal hyperplasia. Wall shear stress is generated on the internal wall of a blood vessel by flow adjacent to the wall. Higher levels of wall shear stress have been associated with a reduction in levels of in-stent restenosis.

The expandable element may comprise an inflatable element. Preferably the inflatable element comprises a balloon. The balloon may have one or more longitudinal end parts as discussed above.

The expandable element may be configured to at least partially expand a stent. Preferably in the expanded configuration the expandable element is configured to exert force via a stent on the internal wall of a blood vessel. The expandable element may be configured to expand a stent having a longitudinal axis which curves in three-dimensional space. The expandable element may be configured to expand a stent having a longitudinal axis which is substantially straight. Ideally the device comprises a stent deployment device.

Alternatively, the stent with a longitudinal axis which curves in three-dimensional space may have been deployed at a previous time and the expandable element is configured to exert force on the stent to recreate or reinforce this shape, should the shape have become less defined over time, or if the three dimensional shape is not adequate from the outset (i.e. if shape only partially taken up by vessel on implantation of the stent).

Most preferably the device comprises means to align the expandable element with a stent or blood vessel lumen. In the case of a three-dimensional curved stent it is particularly important to ensure the stent is correctly aligned with the three-dimensional curve of the expandable element. The alignment means may comprise means to visualise the expandable element. The alignment means may be arranged to assist rotational alignment of the expandable element with the stent. The alignment means may be arranged to assist axial alignment of the expandable element with the stent. Preferably the alignment means is arranged to assist rotational and axial alignment. Preferably the alignment means comprises one or more markers on the expandable element.

The markers may comprise radiopaque material such as tantalum, platinum, gold or iridium. The markers may be located on diametrically opposite sides, of the expandable element, such that when an x-ray source is applied to the expandable element inserted in the stent, the x-ray image produced can be used to determine the orientation of the expandable element. For example, an image showing both markers may indicate the expandable element is out of alignment, whilst an image showing only one marker (the other being in the shadow of the first) indicates the expandable element is aligned.

In another embodiment, the alignment means extends circumferentially and/or longitudinally along at least part of the expandable element, for example in a cross or partial cross shape.

Preferably, the stent is also provided with markers, which are located so as to be positioned in a predetermined way relative to the markers on the stent when the expandable element is correctly aligned within the stent. For example, the stent can be provided with radiopaque markers which line up with those on the expandable element when the latter is correctly aligned.

In another embodiment markers are provided on both the expandable element and the stent such that when the expandable element is inserted inside the collapsed stent, the markers can be used to achieve correct alignment. For example the markers on the expandable element and the stent may match up. The markers may also be used to achieve correct alignment between the expandable element and the stent when the stent has been inserted in the body and the expandable element is expanded within the stent.

However, in some cases, due to the small size of the delivery system involved in transluminal procedures, it might be difficult to distinguish individual markers on devices. For example, it might be difficult to view the rotational orientation of an asymmetric marker such as an "L" on an expandable element. With this in mind, an embodiment of the invention provides another alternative alignment means. In this embodiment, the expandable element comprises a varying cross section. When inflated with saline or a contrast enhancing medium (radiopaque dye), the varying cross-section of the expandable element will be visible when viewed using fluoroscopy (the use of a radiopaque dye in particular to fill the expandable element aids its visualisation during inflation and positioning). The varying cross section can be used to determine the rotational orientation of the expandable element and thus enable it to be deployed correctly. The expandable element may be deployed and aligned in a blood vessel or stent within a blood vessel in-vivo, or deployed and aligned in a stent ex-vivo prior to insertion in the body.

Using the capability of the c-arm on a fluoroscope, for example, the expandable element can be viewed in two orthogonal directions, for example in elevation (lateral) and plan (anterior posterior) view. In this way, the orientation of the varying or notched cross-section of the expandable element can be determined whilst it is inserted into a vessel or stent within the body, and thus the expandable element can be orientated correctly with respect to the curvature of the stent or vessel lumen.

The cross section may vary in any way that enables the orientation of the expandable element to be identified. For example, the variation may be such that a projection view of the cross section of the expandable element varies as the expandable element is rotated. In one embodiment the variation in cross section preferably comprises a notch, which may be any shape or indentation in the outer surface of the expandable element. Such a notch preferably has first order rotational symmetry. Preferably a notch comprises a substantially flat portion recessed in the outer surface of the expandable element.

In one embodiment, a stent is provided with at least one reference point, for example a radiopaque marker, which is arranged to line up with the varying cross section (or a portion thereof) of the expandable element in a pre-determined manner when the expandable element is correctly deployed. In one embodiment, radiopaque markers are positioned so as to match with the notched portions of the expandable element when the expandable element is rotated and deployed correctly. The markers can be any shape, but are preferably elliptical or rectangular. Suitable radiopaque materials are tantalum, platinum, gold or iridium.

The variation in cross section, for example a notched portion, preferably aligns uniquely in only one way with a marker on a stent. Thus, once alignment with the marker is achieved, rotational alignment with the stent is also achieved.

In one embodiment, two radiopaque markers are provided, one towards each end of the stent. However the markers are more preferably provided in pairs, each pair comprising two markers arranged diametrically opposite, i.e. 180° apart, around the circumference of the stent. In another embodiment multiple pairs are provided at the same longitudinal position on the stent, each pair being arranged diametrically opposite and being distinguishable from other pairs. For example two pairs of markers may be provided, each of the four markers being separated by 90°.

Thus, as can be seen, the above described alignment means ensures that a certain rotational orientation of the expandable element with respect to the stent or vessel geometry is achieved when deployed.

Whilst this alignment means is particularly useful to assist the positioning of an expandable element having a longitudinal axis curved in three-dimensional space, in accordance with present invention, it is also useful for aligning other expandable elements. Therefore, it is seen as an invention in its own right.

Thus, viewed from another aspect, the invention provides a medical device comprising: an expandable element for location in a blood vessel; the expandable element being movable between a collapsed configuration and an expanded configuration; and wherein the expandable element is provided with a varying or notched cross section that assists with aligning the expandable element within the blood vessel.

This device may assist with aligning the expandable element directly within the vessel i.e. without the presence of a stent, or it may assist with aligning the expandable element within a stent within a vessel.

The expandable element may have a centreline that is straight or curved in two or three dimensions. The stent or blood vessel may have a straight or corresponding curved centreline. Preferably the varying or notched cross section enables the rotational orientation of the expandable element to be correctly matched with the curvature of the stent or blood vessel. The cross section may vary in any way that enables the orientation of the expandable element to be identified. For example, the variation may be such that a projection view of the cross section of the expandable element varies as the expandable element is rotated. A notch may be any shape or indentation in the outer surface of the expandable element. Preferably a notch comprises a substantially flat portion recessed in the outer surface of the expandable element. One such notch is preferably provided towards each end of the expandable element. Radiopaque markers may be provided on a stent, positioned so as to match up with the notches when the expandable element is correctly aligned.

In yet another aspect, the invention provides a method for treating a blood vessel, the method comprising the steps of: locating an expandable element in the blood vessel; moving the expandable element from a collapsed configuration to an expanded configuration; and aligning the expandable element within the blood vessel or a stent located within the blood vessel using a portion of the expandable element having a varying or notched cross section. This is therefore an in-vivo procedure, carried out inside the body.

In another aspect, the invention provides: a method of manufacturing a medical device comprising: locating an expandable element in a stent; and aligning the expandable element within the stent using markers on or a varying cross section of the expandable element. Preferably markers on the stent are also used to align the expandable element. This is an ex-vivo procedure, carried out outside the body.

Preferably, the step of aligning comprises aligning the varying or notched cross section portion with a corresponding reference point on the stent.

Preferably, in the expanded configuration of the expandable element, the expandable element is configured to exert force, via a stent in which it is inserted, on the internal wall of a blood vessel to deform the internal wall of the blood vessel such that the longitudinal axis of the blood vessel is caused to curve in three-dimensional space.

In one embodiment in the expanded configuration the expandable element is configured to contact the internal wall of a blood vessel directly, i.e. no stent is used. Preferably the device comprises a dilation device.

In one case the device comprises an elongate element upon which the expandable element is mounted.

The device of the invention may be employed as a stent delivery device, and/or as a stent deployment device, and/or as a post dilatation device.

In another aspect of the invention there is provided a medical system comprising:—
a medical device of the invention, and
a stent suitable for deployment in a blood vessel to support at least part of the internal wall of the blood vessel.

In one embodiment of the invention the stent is movable between a delivery configuration and a deployed configuration. Preferably the stent is collapsed in the delivery configuration. This low-profile arrangement provides for ease of delivery. Ideally in the delivery configuration at least part of the longitudinal axis of the stent is substantially straight. Most preferably the stent is expanded in the deployed configuration. In the deployed configuration at least part of the longitudinal axis of the stent may be curved in three-dimensional space. Preferably in the deployed configuration the stent is configured to exert force on the internal wall of a blood vessel causing the longitudinal axis of the blood vessel to curve in three-dimensional space. Blood flowing through the three-dimensional curved part of the blood vessel undergoes a swirling action. The swirling flow of blood has been found to minimise thrombosis and platelet adhesion, and to minimise or prevent coverage of the stent by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia.

In one case the stent is movable between the delivery configuration and an intermediate configuration, and between the intermediate configuration and the deployed configuration. Preferably the stent is at least partially expanded in the intermediate configuration. In the intermediate configuration at least part of the longitudinal axis of the stent may be substantially straight. In the intermediate configuration at least part of the longitudinal axis of the stent may be curved in three-dimensional space.

The invention also provides in another aspect a method for treating a blood vessel, the method comprising the steps of:—
locating an expandable element in the blood vessel, and moving the expandable element from a collapsed configuration to an expanded configuration in which at least part of the longitudinal axis of the expandable element is curved in three-dimensional space.

In one embodiment of the invention the expandable element exerts force on the internal wall of the blood vessel causing the longitudinal axis of the blood vessel to curve in three-dimensional space. Blood flowing through the three-dimensional curved part of the blood vessel undergoes a swirling action. The swirling flow of blood has been found to minimise thrombosis and platelet adhesion, and to minimise or prevent coverage of a stent by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia.

In one case the step of moving the expandable element from the collapsed configuration to the expanded configuration at least partially expands a stent. Preferably the expandable element exerts force via the stent on the internal wall of the blood vessel. Ideally the method comprises the step of moving the stent from a delivery configuration to a deployed configuration. Most preferably the method comprises the step of moving the stent from the delivery configuration to an intermediate configuration, and from the intermediate configuration to the deployed configuration. The invention may provide a method of deploying a stent. Preferably the method comprises the step of aligning the expandable element with a stent. In the case of a three-dimensional curved stent it is important to ensure the stent is correctly aligned with the three-dimensional curve of the expandable element.

In another embodiment the expandable element contacts the internal wall of the blood vessel directly. The invention may provide a method of dilation.

BRIEF DESCRIPTION OF THE DRAWINGS

The invention will be more clearly understood from the following description of some embodiments thereof, given by way of example only, with reference to the accompanying drawings, in which:

FIG. 2(*a*) is an isometric view of the medical device of FIG. 1 in the expanded configuration;

FIG. 3 is a cross-sectional side view of a blood vessel;

FIGS. 4 to 6 are cross-sectional side views illustrating movement of a stent from a delivery configuration to an intermediate configuration in the blood vessel of FIG. 3;

FIGS. 10(*a*) to 10(*e*) are cross-sectional side views illustrating movement of the stent of FIGS. 4 to 10 from the delivery configuration to the deployed configuration using the medical device of FIG. 1;

FIG. 26 illustrates an alignment system of a medical device according to a further embodiment of the invention wherein the expandable element is in a non-aligned configuration;

FIG. 27 illustrates an alignment system of a medical device according to the embodiment of FIG. 26 wherein the expandable element is in an aligned configuration;

FIGS. 30(a)-(c) illustrate a stent and expandable element with a single bend in one direction, provided with alignment means; and FIGS. 31(a)-(c) illustrate a stent and expandable element with three dimensional curvature, provided with alignment means.

DETAILED DESCRIPTION

Figures 1, 2:
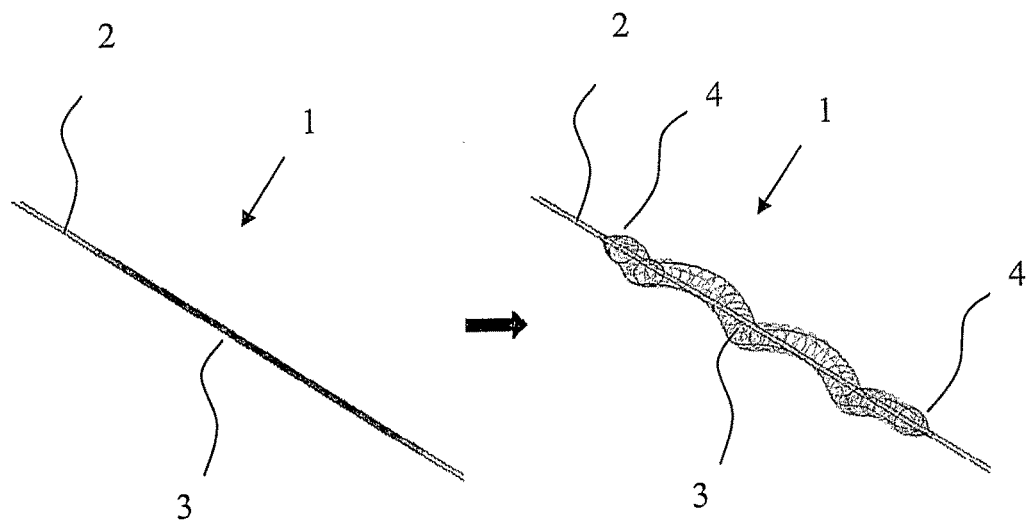
FIG. 1 is an isometric view of a medical device according to the invention in a collapsed configuration.
FIG. 2 is an isometric view of the medical device of FIG. 1 in an expanded configuration.
Figure 2A:
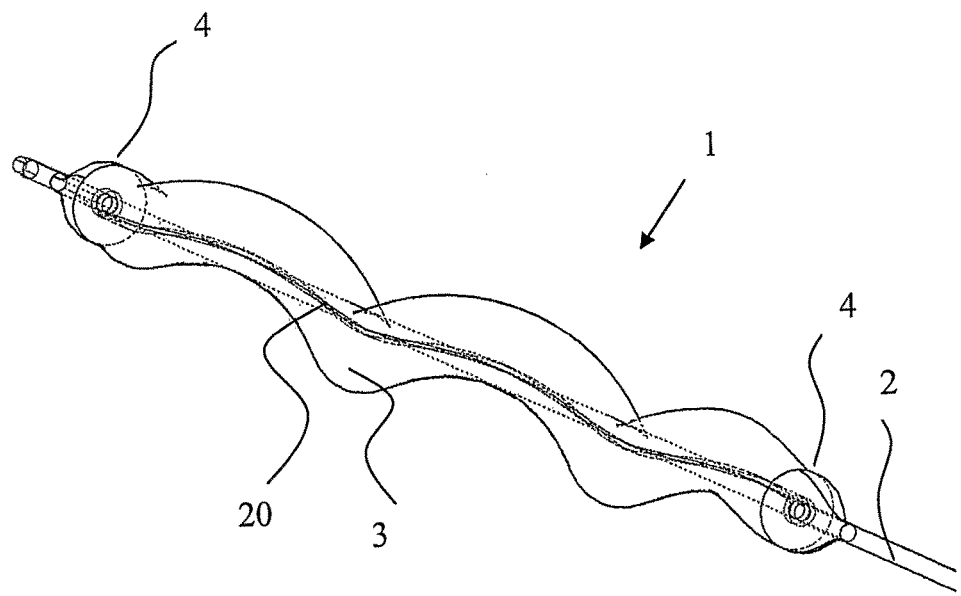

Referring to the drawings, and initially to FIGS. 1 to 2(a) thereof; there is illustrated a medical system according to the invention. In this case the medical system comprises a stent deployment system.

The stent deployment system comprises a stent deployment device 1, and a stent suitable for deployment in a blood vessel 5 to support at least part of the internal wall of the blood vessel 5.

The stent deployment device 1 comprises an elongate catheter shaft 2, and a single expandable element 3 for location in the blood vessel 5. The expandable element 3 is mounted on the catheter shaft 2.

In this case the expandable element 3 comprises an inflatable balloon. The inflatable balloon 3 is movable between a collapsed configuration (FIG. 1) and an expanded configuration (FIG. 2). In the collapsed configuration the longitudinal axis of the balloon 3 is straight, and the balloon 3 is cylindrically shaped. In the expanded configuration part of the longitudinal axis of the balloon 3 is curved in three-dimensional space, and part of the balloon 3 is helically shaped. The balloon has at each end an end part 4 in which the helical angle of the longitudinal axis of the end part increases in a direction away from the end of the balloon.

The balloon 3 is suitable for expanding the stent.

The stent may be a balloon expandable stent 6, as illustrated in FIGS. 3 to 10(e). Alternatively the stent may be a self-expanding stent 7, as illustrated in FIGS. 11 to 18.

Figure 10:
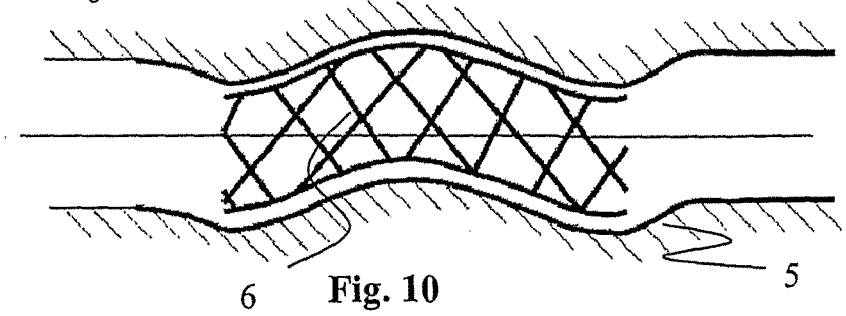
Figure 18:
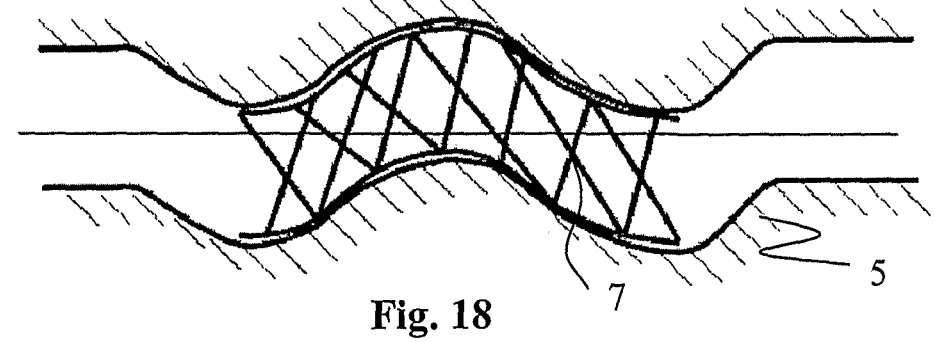

The stent 6, 7 may be movable from a collapsed delivery configuration (FIGS. 4 and 12) to a partially expanded intermediate configuration (FIGS. 6 and 14), and subsequently from the intermediate configuration to a fully expanded deployed configuration (FIGS. 10 and 18). In the delivery configuration the longitudinal axis of the stent 6, 7 is straight. In the deployed configuration the longitudinal axis of the stent 6, 7 is curved in three-dimensional space.

The longitudinal axis of the stent 6 may be straight in the intermediate configuration (FIG. 6). The balloon 3 is suitable for expanding the stent 6 having the straight longitudinal axis. In this case the balloon 3 expands the stent 6 to ensure that in the deployed configuration the longitudinal axis of the stent 6 is curved in three-dimensional space.

Figure 14:
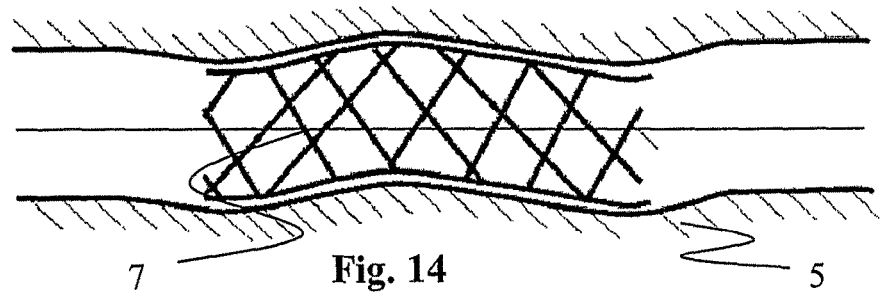

Alternatively the longitudinal axis of the stent 7 may be curved in three-dimensional space in the intermediate configuration (FIG. 14). The balloon 3 is suitable for expanding the stent 7 having the longitudinal axis which curves in three-dimensional space. In this case the balloon 3 expands the stent 7 to ensure that in the deployed configuration the stent 7 is bedded into the internal wall of the blood vessel 5 and the stent 7 has taken up the fully deployed three-dimensional curve. In addition the balloon 3 expands the stent 7 to ensure that the stent amplitude ratio is such that it is not possible for blood to flow through the blood vessel 5 or the stent 7 without undergoing swirling. The amplitude ratio is the ratio of the amplitude of the helical longitudinal axis of the stent to the internal diameter of the stent.

The balloon 3 is inflated to expand the stent 7 enhancing its helical structure, increasing the amplitude ratio, reducing the pitch, anchoring the stent 7 in place, and ensuring good wall apposition.

The stent 6 may be movable directly from the collapsed delivery configuration (FIG. 10(b)) to the fully expanded deployed configuration (FIG. 10(c)) without any intermediate configuration. In the delivery configuration the longitudinal axis of the stent 6 is straight. In the deployed configuration the longitudinal axis of the stent 6 is curved in three-dimensional space.

The balloon 3 is suitable for expanding the stent 6 having the straight longitudinal axis. In this case the balloon 3 expands the stent 6 to ensure that in the deployed configuration the longitudinal axis of the stent 6 is curved in three-dimensional space.

Figure 8:
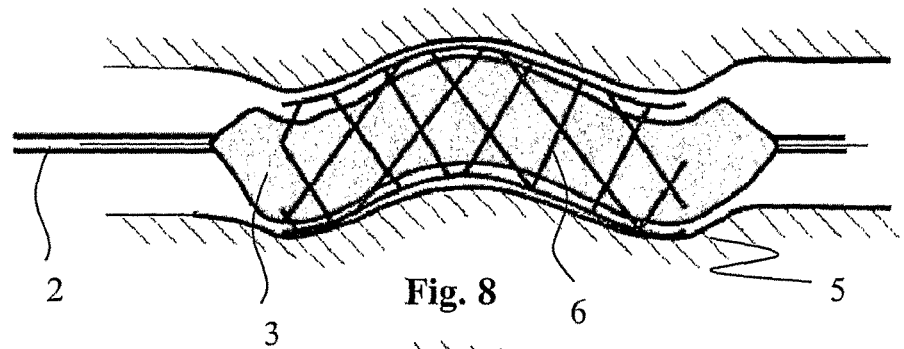
Figure 16:
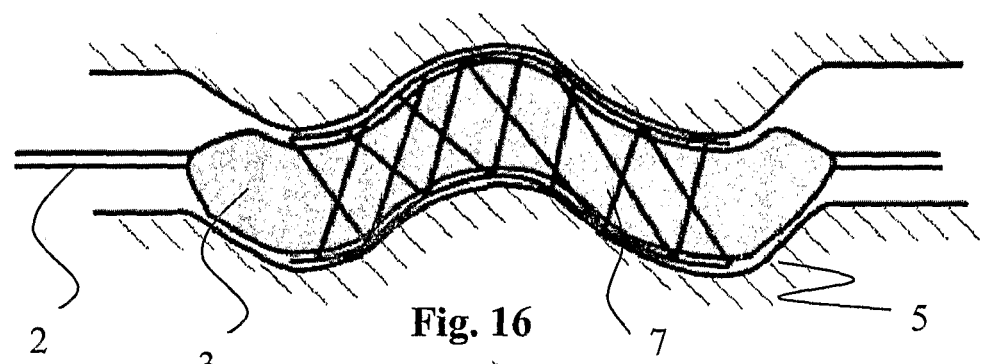

In each case the balloon 3 in the expanded configuration exerts force on the stent 6, 7. In the deployed configuration the stent 6, 7 in turn exerts force on the internal wall of the blood vessel 5 causing the longitudinal axis of the blood vessel 5 to curve in three-dimensional space (FIGS. 8 and 16).

As illustrated in FIG. 2(a), the stent deployment device 1 also comprises visualisation means to align the balloon 3 with the stent 6, 7. In this case the visualisation means comprises a marker 20 on the balloon 3. The marker 20 extends circumferentially and longitudinally along the balloon 3 in a helix or spiral. The marker 20 may be aligned with the helical shape of the stent 6, 7.

FIG. 2(a) illustrates the helical marker 20 on the helical balloon 3.

The stent deployment device 1 may be configured for rapid exchange delivery over a guidewire or over-the-wire delivery over a guidewire.

FIG. 1 illustrates the helical balloon 3 unexpanded on the catheter 2, and FIG. 2 illustrates the helical balloon 3 expanded on the catheter 2.

In use, the stent deployment device 1 may be used to deploy the balloon expandable stent 6 in the blood vessel 5 to support at least part of the internal wall of the blood vessel 5, as illustrated in FIGS. 3 to 10(e). Alternatively the stent deployment device 1 may be used to deploy the self-expanding stent 7 in the blood vessel 5 to support at least part of the internal wall of the blood vessel 5, as illustrated in FIGS. 11 to 18.

In one case the balloon expandable stent 6 is arranged in the delivery configuration mounted to a delivery catheter 8. In the delivery configuration the longitudinal axis of the stent 6 is straight. The delivery catheter 8 comprises an inflatable balloon 9.

The balloon 9 is movable between a collapsed configuration (FIG. 4) and an expanded configuration (FIG. 5). In the collapsed configuration the longitudinal axis of the balloon 9 is straight, and the balloon 9 is cylindrically shaped. In the expanded configuration the longitudinal axis of the balloon 9 is straight, and the balloon 9 is cylindrically shaped.

The delivery catheter 8 and the stent 6 are inserted into the blood vessel 5 and advanced until the stent 6 is located at a desired treatment site 10 (FIG. 4). The balloon 9 is inflated to move the stent 6 from the delivery configuration to the intermediate configuration (FIG. 5). The longitudinal axis of the stent 6 is straight in the intermediate configuration. The balloon 9 is deflated and the delivery catheter 8 is withdrawn (FIG. 6).

Figure 7:
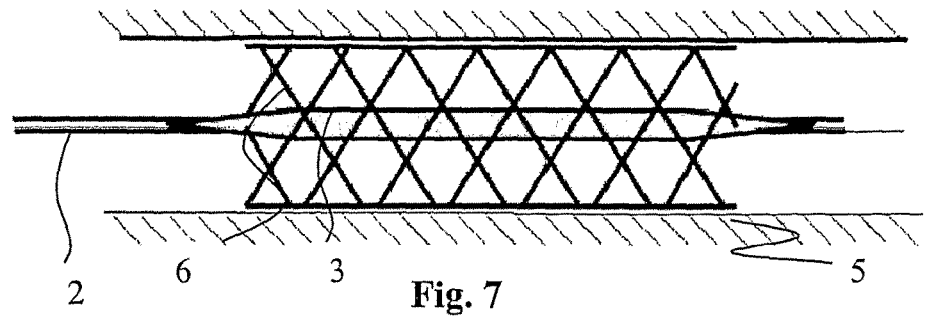
FIGS. 7 to 10 are cross-sectional side views illustrating movement of the stent from the intermediate configuration to a deployed configuration using the medical device of FIG. 1.

The stent deployment device 1 of the invention is then inserted into the blood vessel 5 and advanced until the balloon 3 is aligned with the stent 6 (FIG. 7). The balloon 3 is inflated to expand the stent 6 from the intermediate configuration to the deployed configuration. The balloon 3 in the expanded configuration exerts force on the stent 6 to move the stent 6 from the intermediate configuration to the deployed configuration (FIG. 8). In the deployed configuration the longitudinal axis of the stent 6 is curved in three-dimensional space. In the deployed configuration the stent 6 exerts force on the internal wall of the blood vessel 5 causing the longitudinal axis of the blood vessel 5 to curve in three-dimensional space.

The balloon 3 is deflated (FIG. 9), and the stent deployment device 1 is withdrawn from the blood vessel 5 (FIG. 10). The deployed stent 6 remains in the blood vessel 5.

Blood flowing through the three-dimensional curved blood vessel 5 undergoes a swirling action. The swirling flow of blood has been found to minimise thrombosis and platelet adhesion, and to minimise or prevent coverage of the stent 6 by ingrowth of intima. The flow pattern in the blood vessel 5 including the swirling pattern induced by the non-planar geometry of the blood vessel 5 operates to inhibit the development of vascular diseases such as thrombosis/atherosclerosis and intimal hyperplasia.

Figure 9:
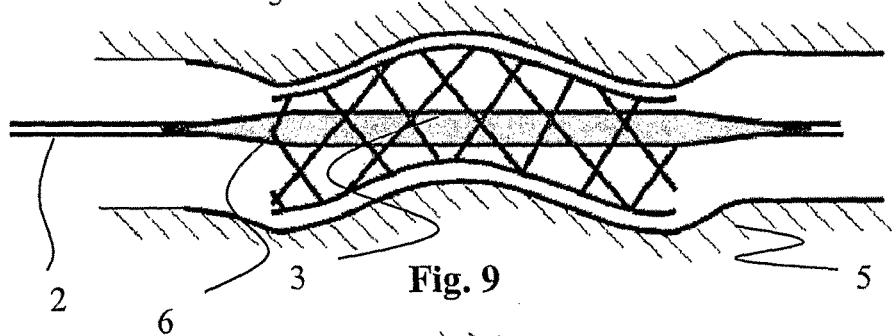

FIGS. 3 to 10 illustrate the balloon expandable straight stent 6 with the 3-D balloon 3. FIG. 3 illustrates the stenosed vessel 10. FIG. 4 illustrates the crimped stent 6 on the delivery system 8. FIG. 5 illustrates the balloon 9 inflated and the stent 6 deployed. FIG. 6 illustrates the vessel patency restored. FIG. 7 illustrates the 3-D balloon catheter 1. FIG. 8 illustrates the 3-D balloon 3 inflated. FIG. 9 illustrates the 3-D balloon 3 deflated for withdrawal. FIG. 10 illustrates the stent 6 and the blood vessel 5 deformed to assume the 3-D curvature.

In another case the balloon expandable stent 6 is arranged in the delivery configuration mounted to the stent deployment device 1 of the invention. In the delivery configuration the longitudinal axis of the stent 6 is straight.

The stent deployment device 1 and the stent 6 are inserted into the blood vessel 5 and advanced until the stent 6 is located at a desired treatment site 10 (FIG. 10(*b*)). The balloon 3 is inflated to expand the stent 6 from the delivery configuration to the deployed configuration (FIG. 10(*c*)). The balloon 3 in the expanded configuration exerts force on the stent 6 to move the stent 6 from the delivery configuration to the deployed configuration. In the deployed configuration the longitudinal axis of the stent 6 is curved in three-dimensional space. In the deployed configuration the stent 6 exerts force on the internal wall of the blood vessel 5 causing the longitudinal axis of the blood vessel 5 to curve in three-dimensional space.

The balloon 3 is deflated (FIG. 10(*d*)), and the stent deployment device 1 is withdrawn from the blood vessel 5 (FIG. 10(*e*)). The deployed stent 6 remains in the blood vessel 5.

Blood flowing through the three-dimensional curved blood vessel 5 undergoes a swirling action. The swirling flow of blood has been found to minimise thrombosis and platelet adhesion, and to minimise or prevent coverage of the stent 6 by ingrowth of intima. The flow pattern in the blood vessel 5 including the swirling pattern induced by the non-planar geometry of the blood vessel 5 operates to inhibit the development of vascular diseases such as thrombosis/atherosclerosis and intimal hyperplasia.

FIGS. 10(*a*) to 10(*e*) illustrate the straight stent 6 crimped onto the helical balloon 3.

In the case of the self-expanding stent 7, the stent 7 is arranged in the delivery configuration constrained within a delivery sheath 11. In the delivery configuration the longitudinal axis of the stent 7 is straight.

Figure 11:
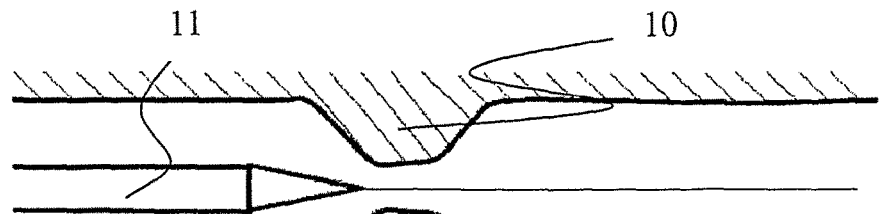
FIGS. 11 to 14 are cross-sectional side views illustrating movement of another stent from a delivery configuration to an intermediate configuration in the blood vessel of FIG. 3.
Figure 12:
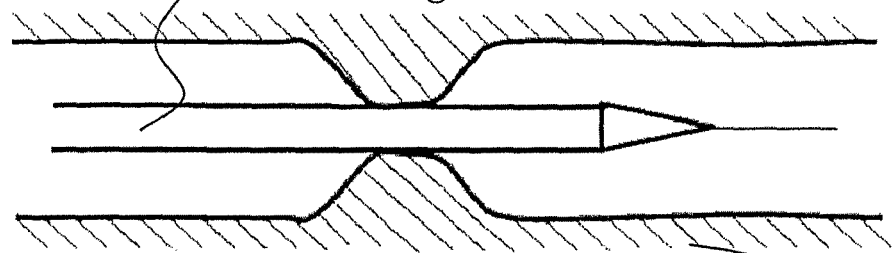
Figure 13:
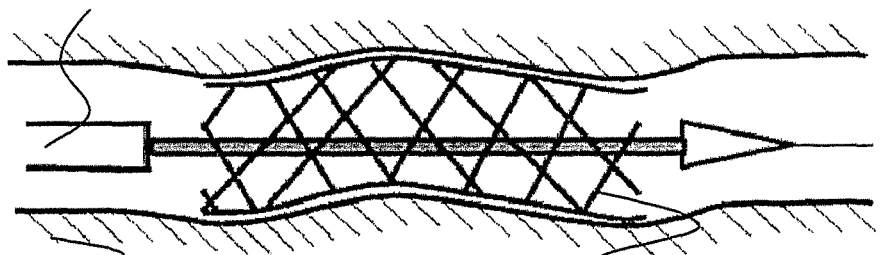

The delivery sheath 11 and the stent 7 are inserted into the blood vessel 5 and advanced until the stent 7 is located at the desired treatment site 10 (FIGS. 11 and 12). The sheath 11 is retracted to enable the stent 7 to move from the delivery configuration to the intermediate configuration (FIG. 13). The longitudinal axis of the stent 7 is curved in three-dimensional space in the intermediate configuration. In the intermediate configuration the stent 7 exerts force on the internal wall of the blood vessel 5 causing the longitudinal axis of the blood vessel 5 to curve in three-dimensional space. The delivery sheath 11 is withdrawn (FIG. 14).

Figure 15:
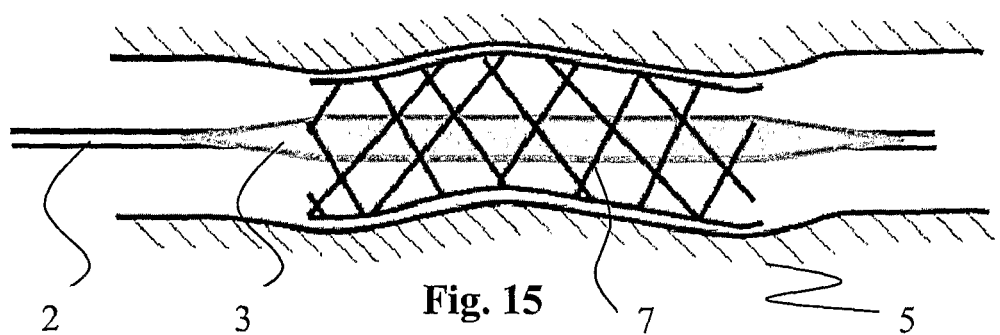
FIGS. 15 to 18 are cross-sectional side views illustrating movement of the stent from the intermediate configuration to a deployed configuration using the medical device of FIG. 1.

The stent deployment device 1 of the invention is then inserted into the blood vessel and advanced until the balloon 3 is aligned with the stent 7 (FIG. 15). The balloon 3 is inflated to expand the stent 7 from the intermediate configuration to the deployed configuration. The balloon 3 in the expanded configuration exerts force on the stent 7 to move the stent 7 from the intermediate configuration to the deployed configuration (FIG. 16). In the deployed configuration the longitudinal axis of the stent 7 is further curved in three-dimensional space. In the deployed configuration the stent 7 exerts further force on the internal wall of the blood vessel 5 causing the longitudinal axis of the blood vessel 5 to curve further in three-dimensional space.

The balloon 3 is deflated (FIG. 17), and the stent deployment device 1 is withdrawn from the blood vessel 5 (FIG. 18).

Blood flowing through the three-dimensional curved blood vessel 5 undergoes a swirling action. The swirling flow of blood has been found to minimise thrombosis and platelet adhesion, and to minimise or prevent coverage of the stent 7 by ingrowth of intima. The flow pattern in the blood vessel 5 including the swirling pattern induced by the non-planar geometry of the blood vessel 5 operates to inhibit the development of vascular diseases such as thrombosis/atherosclerosis and intimal hyperplasia.

Figure 17:
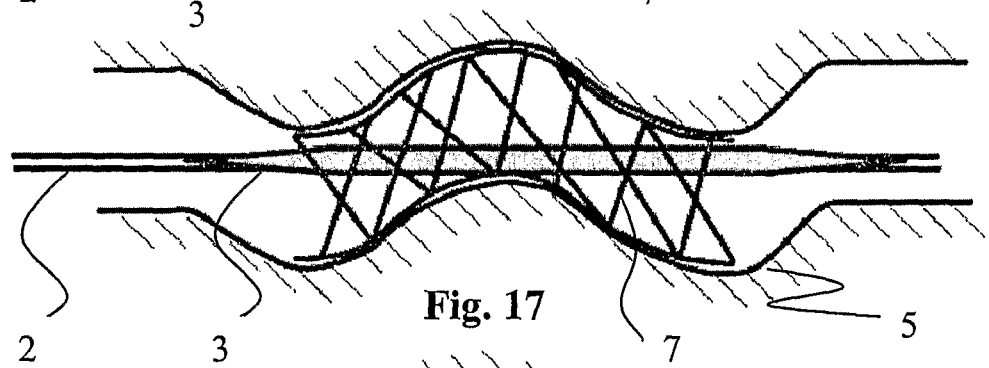

FIGS. 11 to 18 illustrate the 3-D stent 7 with the 3-D balloon 3. FIG. 11 illustrates the stenosed vessel 10 and the stent delivery system 11. FIG. 13 illustrates the 3-D stent 7 deployed. FIG. 14 illustrates the blood vessel 5 remodeled to take the 3-D curvature. FIG. 15 illustrates the balloon catheter 1. FIG. 17 illustrates the 3-D balloon 3 deflated for withdrawal. FIG. 18 illustrates the balloon 3 withdrawn, and the stent 7 with maximised 3-D curvature in place.

Figure 19:
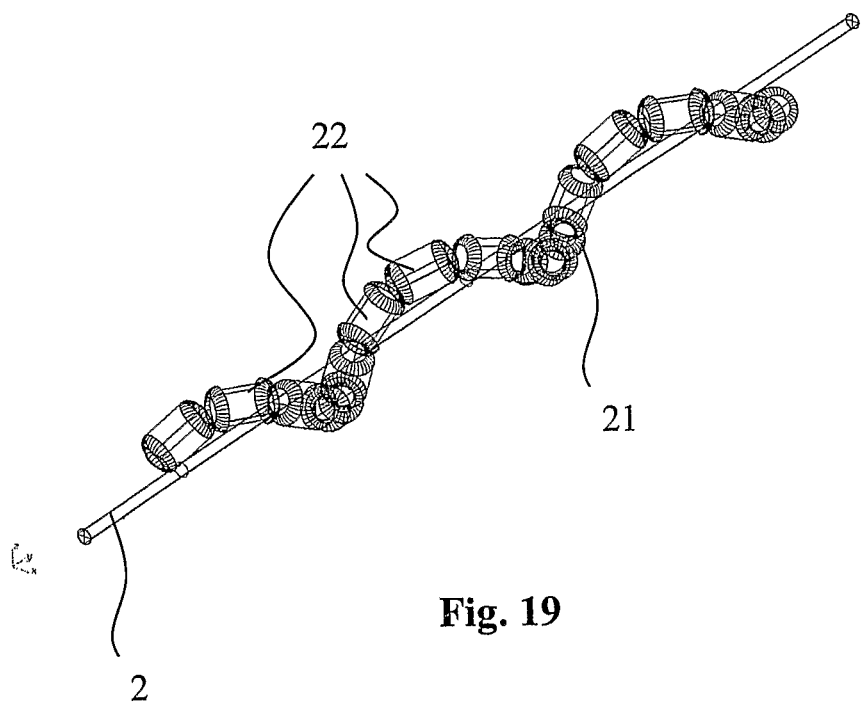
FIG. 19 is an isometric view of another medical device according to the invention in an expanded configuration.
Figure 20:
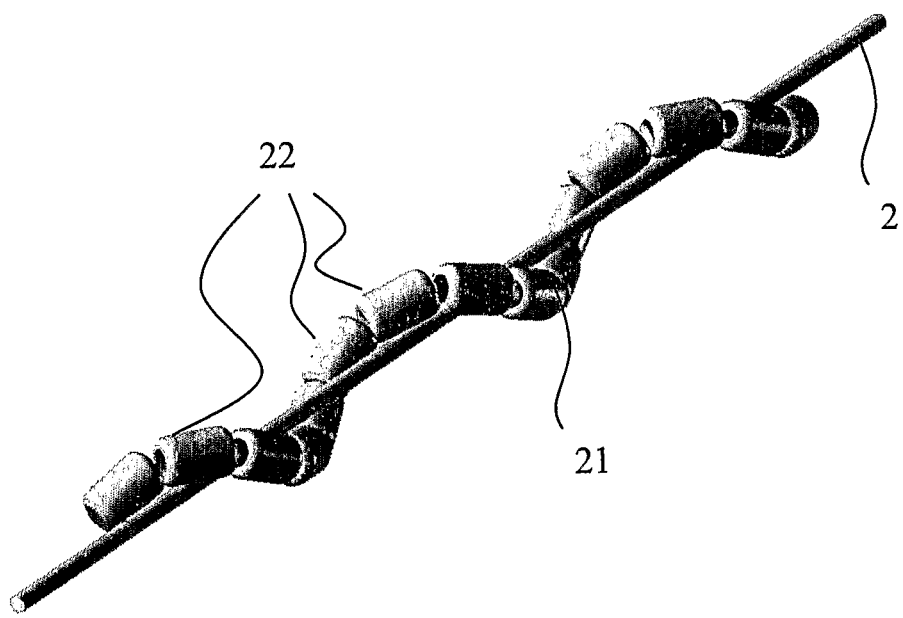
FIG. 20 is an isometric view of the medical device of FIG. 19 in the expanded configuration.

It will be appreciated that the expandable element 21 may comprise a plurality of separate expandable members 22, as illustrated in FIGS. 19 and 20. In the expanded configuration the overall longitudinal axis of the expandable element 21 is curved in three-dimensional space, and the expandable element 21 is helically shaped overall. In the expanded configuration the longitudinal axis of each expandable member 22 is straight, and each expandable member 22 is cylindrically shaped. The expandable element 21 has a piecewise three dimensional curved shape. FIGS. 19 and 20 illustrate the piecewise balloon 21 comprised of the plurality of straight balloons 22.

It will also be appreciated that the expandable element may have alternative shapes, for example in the expanded configuration part of the expandable element may be spiral shaped. The pitch of the spiral may be constant along the length of the expandable element, or may vary along the length of the expandable element.

It will further be appreciated that the stent deployment device may comprise a variety of possible visualisation means to align the expandable element with a stent.

Figure 21:
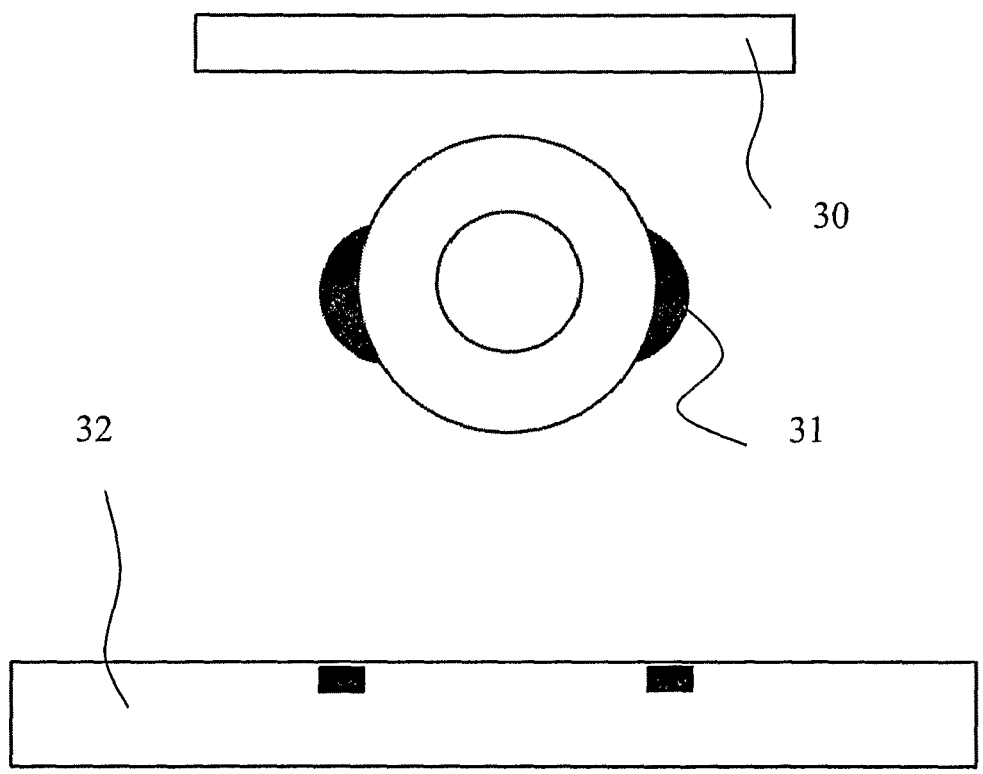
FIG. 21 is an end view of another medical device according to the invention in a non-aligned configuration.
Figure 22:
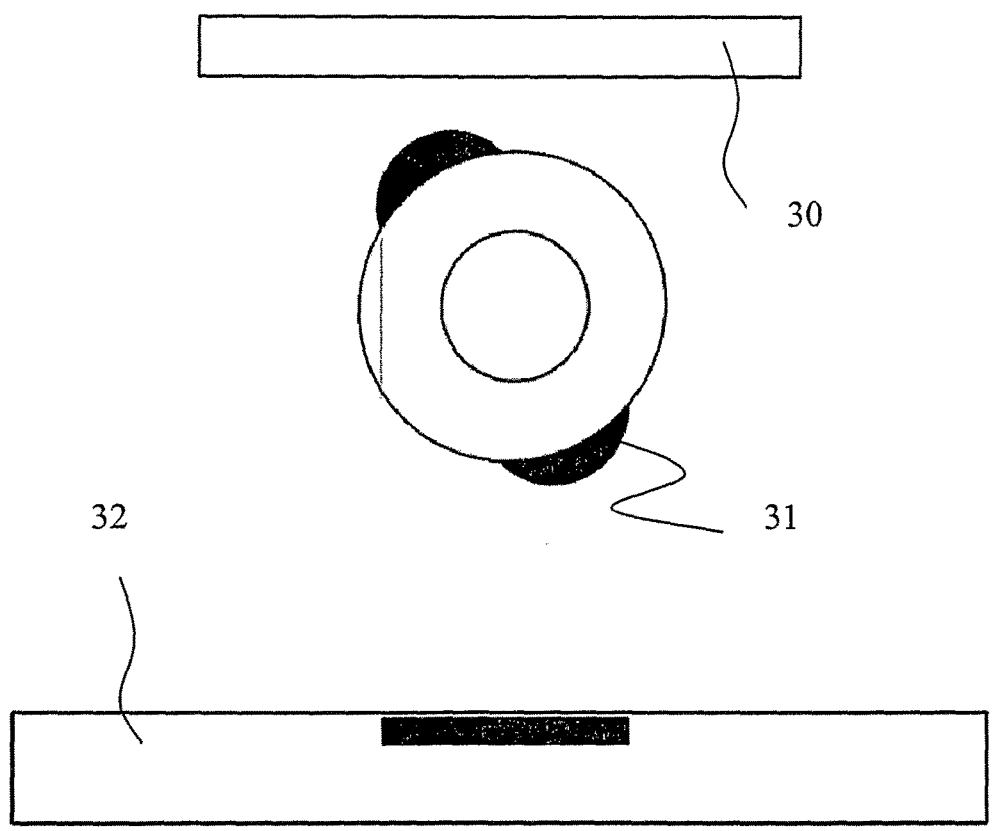
FIG. 22 is an end view of the medical device of FIG. 21 in a semi-aligned configuration.
Figure 23:
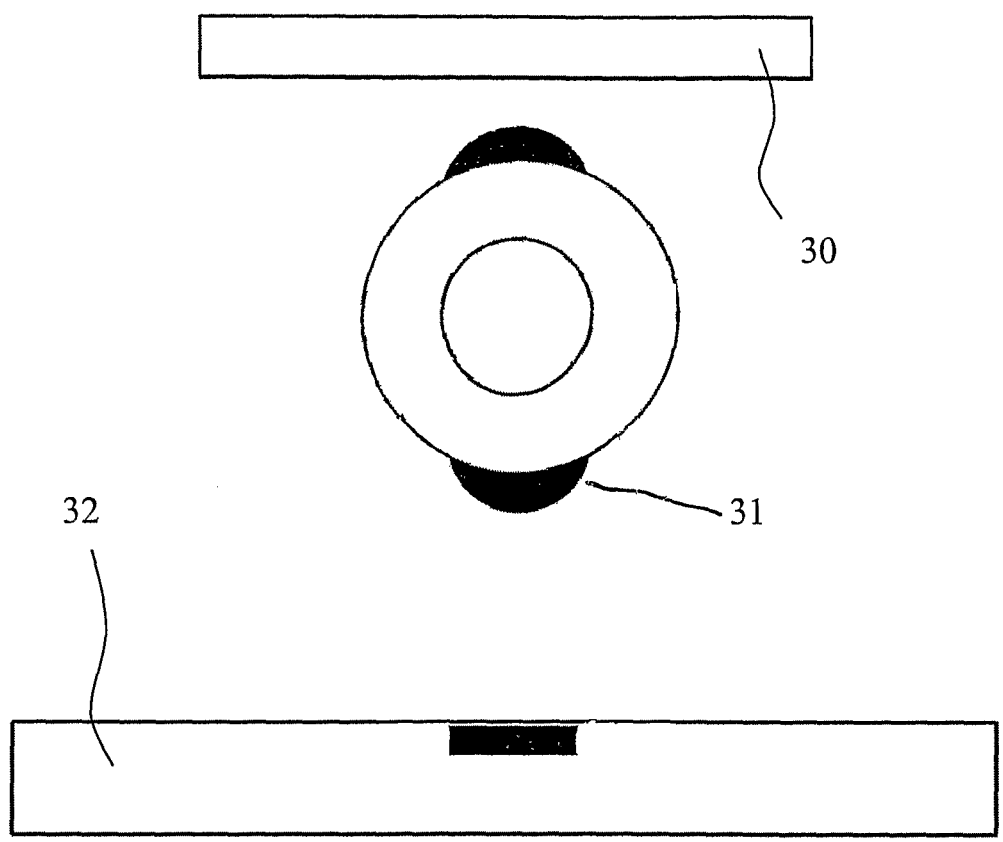
FIG. 23 is an end view of the medical device of FIGS. 21 and 22 in an aligned configuration.

For example FIGS. 21-23 illustrate visualisation means comprising alignment markers. The system utilises fluoroscopy, and includes an x-ray source 30, markers 31 located on an expandable element and imaging media 32. A stent (not illustrated) is located around the expandable element. The markers comprise a radiopaque material. FIG. 21 shows the expandable element before alignment. The extent of alignment is indicated by the image produced by imaging media 32. This embodiment has been devised so that the image shown in FIG. 21, i.e. two small marks, indicates an unaligned state. FIG. 22 illustrates the expandable element having been rotated towards an aligned position, as indicated by the single wide mark on the imaging media 32. FIG. 23 illustrates the expandable element aligned with the stent, as indicated by the single narrower mark on the imaging media 32.

Figure 24:
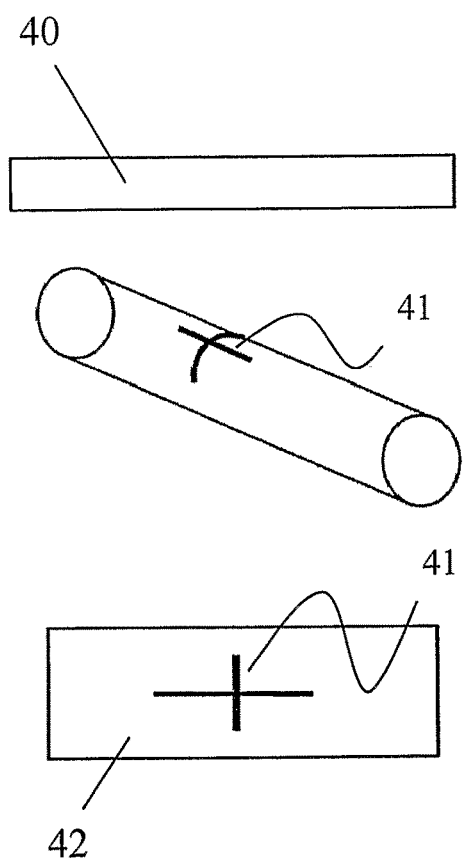
FIG. 24 illustrates an alignment system of a medical device according to an embodiment of the invention wherein the expandable element is in a non-aligned configuration.
Figure 25:
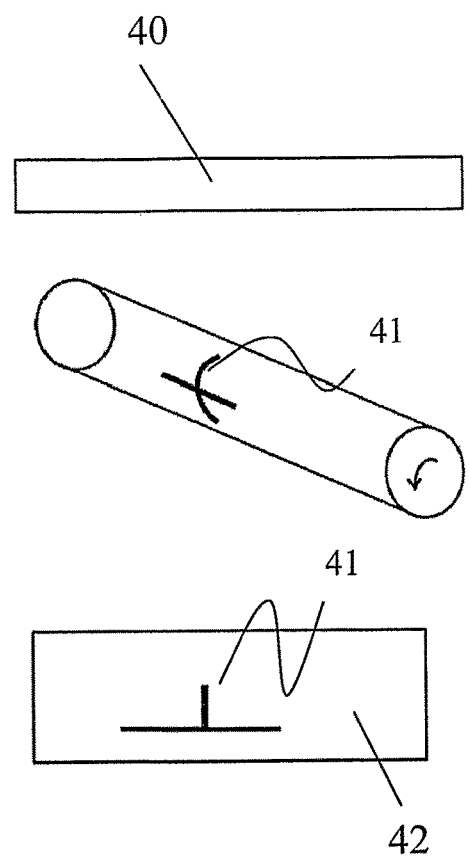
FIG. 25 illustrates an alignment system of a medical device according to the embodiment of FIG. 24 wherein the expandable element is in an aligned configuration.

FIGS. 24 and 25 illustrate a further embodiment comprising a cross shaped alignment marker 41 on an expandable element. As shown in FIG. 24, when viewed utilising fluoroscopy on the imaging media 42 using x-ray source 40, the marker 41 appears as a cross in the first orientation of the expandable element. When the expandable element is rotated into the correct alignment as shown in FIG. 25, the marker 41 will appear as a T-shape on the imaging media 42.

FIGS. 26 and 27 illustrate a further embodiment comprising a T shaped alignment marker 43 on an expandable element. As shown in FIG. 26, when viewed on the imaging media 42 using x-ray source 40 the marker 43 appears as a T in the first orientation of the expandable element. When the expandable element is rotated into the correct alignment as shown in FIG. 27, the marker 41 will appear to have been rotated by 180 degrees.

It will also be appreciated that the medical system according to the invention may comprise a dilation system. The dilation system comprises a dilation device for dilating a blood vessel. The dilation device comprises the elongate catheter shaft, and the single expandable element for location in the blood vessel. In the expanded configuration the expandable element contacts the internal wall of the blood vessel directly.

FIGS. 28 to 31 illustrate an alternative means for aligning the expandable element with a stent, or, in the case of a dilation system, directly with the blood vessel lumen.

Figure 28A:
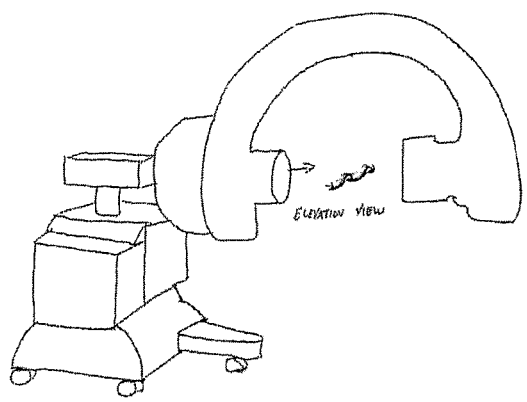
FIG. 28(a) illustrates a fluoroscope and 28(b) is an elevation view of a medical device having notched portions to aid alignment, when viewed with the fluoroscope.
Figure 28B:
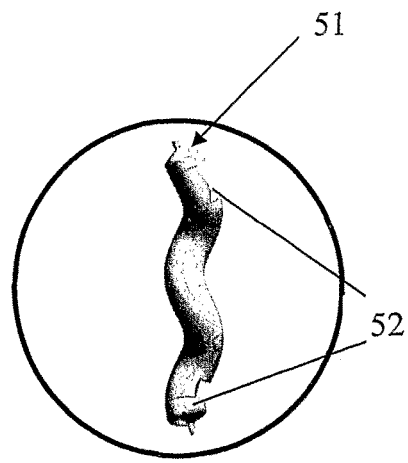
Figure 29A:
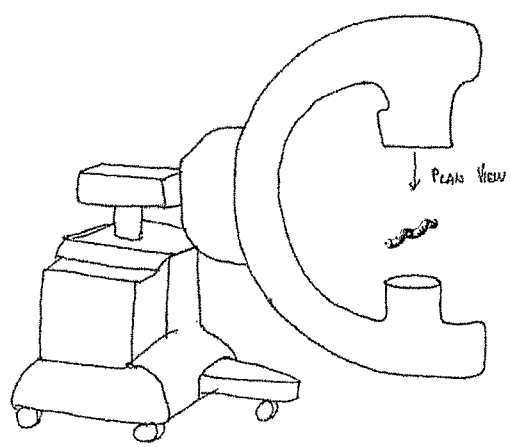
FIG. 29(a) illustrates a fluoroscope and 29(b) is a plan view of the medical device of FIG. 28(b) having notched portions to aid alignment, when viewed with the fluoroscope.
Figure 29B:
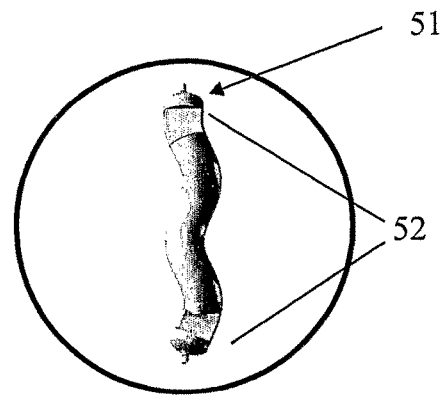

FIGS. 28(b) and 29(b) illustrate an expandable element 51 in vivo in a body (not illustrated) including alignment means. FIG. 28(b) is an elevation (lateral) projection as viewed using the C-arm of a fluoroscope as illustrated in FIG. 28(a). FIG. 29(b) is a plan (anterior-posterior) projection as viewed using the C-arm of a fluoroscope as illustrated in FIG. 29(a). As can be seen, the expandable element 51 has a generally cylindrical cross section, and comprises a generally flat notch section 52 near each end.

In use, when the expandable element 51 is inflated with saline or a contrast enhancing medium (radiopaque dye), the flat notch sections 52 will be visible when viewered using fluoroscopy. Using the capability of the c-arm on a fluoroscope (see FIGS. 28(a) and 29(a)), it is possible to image the expandable element 51 in two orthogonal views to aid positioning, e.g. in elevation and plan views as shown in FIGS. 28(b) and 29(b) respectively. The orientation of the expandable element 51 can be adjusted in vivo to the correct position (i.e. in alignment with the curvature of the stent or blood vessel lumen) based on the orientation of the flat notched sections 52 with respect to another reference point, such as a marker on a self expanding stent, or the curvature of the stent/vessel lumen. The use of a marker is described further with reference to FIGS. 30(a)-(c) and 31(a)-(c).

FIGS. 30(a)-(c) illustrate a stent 60 and expandable element 61 having a single bend in one direction (i.e. a centreline curved in one dimension). FIG. 30(a) illustrates the stent 60. This comprises a pair of diametrically opposed radiopaque markers 63 near each end (only one of each pair is illustrated). FIGS. 30(b) and (c) show the expandable element 61 inserted in the stent 60; FIG. 30(b) being an elevation view and FIG. 30(c) being a plan view. As can be seen, the expandable element 61 comprises flat notched sections 62 as described previously above. The radiopaque markers 63 are positioned so as to match up with the flat notched sections 62 when the expandable element is correctly aligned.

Thus, in use, fluoroscopy can be used to view the expandable element 61, for example in two orthogonal directions such as elevation and plan view, in order to align the notches 62 with the radiopaque markers 63 and thus position the expandable element 61 correctly.

FIGS. 31(a)-(c) are similar to FIGS. 30(a)-(c) but illustrate a stent 70 and expandable element 71 having longitudinal axes curved in three-dimensional space. FIG. 31(a) illustrates the stent 70. This comprises a pair of diametrically opposed radiopaque markers 73 near each end (only one of each pair is illustrated). FIGS. 31(b) and (c) show the expandable element 71 inserted in the stent 70; FIG. 31(b) being an elevation view and FIG. 31(c) being a plan view. As can be seen, the expandable element 71 comprises flat notched sections 72 as described previously above. The radiopaque markers 73 are positioned so as to match up with the flat notched sections 72 when the expandable element is correctly aligned.

Thus, as with the embodiment of FIG. 30 above, in use, fluoroscopy can be used to view the expandable element 71, for example in two orthogonal directions such as elevation and plan view. The notches 72 can then be aligned with the radiopaque markers 73 in order to position the expandable element 71 correctly with respect to the curvature of the stent 70.

The invention is not limited to the embodiments hereinbefore described, with reference to the accompanying drawings, which may be varied in construction and detail.

The invention claimed is:

1. A medical device comprising:
   a balloon for location in a blood vessel,
   the balloon being inflatable between a collapsed configuration and an expanded configuration,
   wherein the balloon has an outer surface and wherein the balloon is provided with a varying cross section for assisting with a rotational alignment of the balloon within the blood vessel or a stent located within the blood vessel wherein the varying cross section comprises an indentation in the outer surface of the balloon wherein the balloon has an otherwise substantially circular cross-section, said indentation being in the outer surface of the balloon where that outer surface expands when the balloon is inflated from the collapsed configuration into the expanded configuration, such that in the expanded configuration, an expanded portion of the balloon comprises the indentation in the outer surface of the balloon.

2. A device as claimed in claim 1, wherein the varying cross section comprises a portion with first order rotational symmetry.

3. A device as claimed in claim 1, wherein the balloon has a longitudinal axis, and wherein in an expanded configuration of the balloon at least part of the longitudinal axis is curved in three-dimensional space.

4. A device as claimed in claim 1, wherein in an expanded configuration of the balloon, the balloon is configured to exert force, directly or via a stent in which it is inserted, on the internal wall of a blood vessel to deform the internal wall of the blood vessel such that the longitudinal axis of the blood vessel is caused to curve in three-dimensional space.

5. A device as claimed in claim 1, wherein at least one longitudinal end part of the balloon has a helical angle which varies along the length of the end part.

6. A method for treating a blood vessel, the method comprising the steps of:
locating a balloon having an outer surface in the blood vessel, the balloon outer surface having a variation in cross section whereby the balloon is provided with a portion of varying cross section comprising an indentation in an otherwise substantially circular cross-section;
inflating the balloon from a collapsed configuration to an expanded configuration;
visualizing the portion of varying cross section in order to determine the rotational orientation of the portion; and
rotating the balloon to rotationally align the balloon within the blood vessel or within a stent located within the blood vessel using the visualized portion having the varying cross section as a guide.

7. A method as claimed in claim 6 wherein the step of aligning comprises aligning the balloon within a stent by aligning the varying cross section portion with a corresponding reference point on the stent.

8. A method as claimed in claim 6 wherein the reference point comprises a radiopaque marker located so as to be positioned in a predetermined way relative to the varying cross-section portion when the balloon is correctly aligned within the stent.

9. A method as claimed in claim 8 wherein at least two pairs of radiopaque markers are provided, each pair comprising two markers arranged diametrically opposite each other around the circumference of the stent.

10. A method as claimed in claim 6 wherein the varying cross section portion has first order rotational symmetry.

11. A method as claimed in claim 6 wherein the step of aligning comprises rotating the balloon, wherein a projection view of the cross section changing during rotation such that the rotational orientation of the balloon can be determined.

12. A method as claimed in claim 6 wherein the varying cross section comprises a notched portion, the notch being an indentation in the outer surface of the balloon, the notch comprising a substantially flat portion recessed in the outer surface of the balloon.

13. A method as claimed in claim 6, wherein the balloon has a longitudinal axis, and wherein in an expanded configuration of the balloon at least part of the longitudinal axis is curved in three-dimensional space.

14. A method as claimed in claim 6, wherein inflating the balloon from a collapsed configuration to an expanded configuration comprises inflating the balloon with a radiopaque dye.

15. A medical device comprising:
a balloon for location in a blood vessel;
the balloon being inflatable between a collapsed configuration and an expanded configuration;
wherein the balloon has an outer surface and opposite ends; and
wherein the balloon outer surface is provided at each end thereof with a portion of varying cross section having first order rotational symmetry, wherein the portion of varying cross section comprises an indentation in an otherwise circular cross section of the balloon.

16. A medical device comprising a balloon for location in a blood vessel; the balloon being inflatable between a collapsed configuration and an expanded configuration; wherein, when the balloon is in the expanded configuration, a projection view of the cross section of the balloon where expanded includes a flat portion which forms an indentation in an outer surface of the balloon, the indentation being located in an otherwise circular cross section of the balloon, whereby the projection view varies as the balloon is rotated such that the rotational orientation of the balloon can be determined to enable the balloon to be correctly rotationally aligned within the blood vessel or a stent located within the blood vessel.

17. A device as claimed in claim 1, wherein the varying cross section of the balloon is a variation from a generally cylindrical cross section of the balloon.

18. A device as claimed in claim 17, wherein the indentation is a flat section of the outer surface of the balloon.

* * * * *